United States Patent

Pigerol et al.

[11] 4,113,736
[45] * Sep. 12, 1978

[54] 2-PHENYL-INDOLE DERIVATIVES

[75] Inventors: Charles Pigerol, Saint-Ouen; Paul de Cointet de Fillain, Sisteron; Souli Nanthavong, Grenoble, all of France

[73] Assignee: S. A. Labaz, Brussels, Belgium

[*] Notice: The portion of the term of this patent subsequent to May 17, 1994, has been disclaimed.

[21] Appl. No.: 667,557

[22] Filed: Mar. 17, 1976

[30] Foreign Application Priority Data

Mar. 21, 1975 [FR] France .................................. 75 08871

[51] Int. Cl.² .................................................. C07D 209/12
[52] U.S. Cl. ............................ 260/326.16; 260/45.8 N
[58] Field of Search ...................................... 260/326.16

[56] References Cited

U.S. PATENT DOCUMENTS

| 3,076,814 | 2/1963 | Speeter et al. | 260/326.16 X |
| 3,352,856 | 11/1967 | Szmuszkovicz | 260/326.16 X |
| 4,024,155 | 5/1977 | Pigerol et al. | 260/326.16 |

OTHER PUBLICATIONS

Buchmann et al., Chemical Abstracts, vol. 60, p. 1682 (1964).
Buchmann et al., Chemical Abstracts, vol. 64, p. 15823 (1966).
Schmitt et al., Chemical Abstracts, vol. 71, 38715r (1969).

Primary Examiner—Dolph H. Torrence
Attorney, Agent, or Firm—Mason, Kolehmainen, Rathburn & Wyss

[57] ABSTRACT

The present invention relates to new stabilizers of polymers and co-polymers of vinyl chloride corresponding to the general formula:

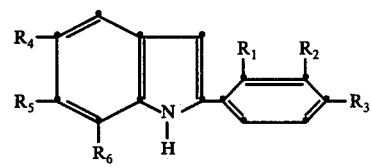

wherein $R_1$, $R_2$, $R_3$, $R_4$, $R_5$ and $R_6$, which are the same or different, represent:

$R_1$ = a hydrogen atom or a branched- or straight-chain alkyloxy group containing from 1 to 12 carbon atoms, $R_2$ = a hydrogen atom, a branched-or straight-chain alkyl group containing from 1 to 3 carbon atoms or a branched- or straight-chain alkyloxy group containing from 1 to 12 carbon atoms, $R_3$ and $R_5$ = a hydrogen atom, a hydroxy group, a branched- or straight-chain alkyl group containing from 1 to 3 carbon atoms or a branched- or straight-chain alkyloxy group containing from 1 to 12 carbon atoms, $R_4$ = a hydrogen atom, a hydroxy group, a branched- or straight-chain alkyl group containing from 1 to 3 carbon atoms or a branched- or straight-chain alkyloxy group containing from 2 to 12 carbon atoms, $R_6$ = a hydrogen atom or a branched- or straight-chain alkyl group containing from 1 to 3 carbon atoms, with the proviso that one at least of the substituents $R_1$, $R_2$, $R_3$, $R_4$, $R_5$ and $R_6$ does not represent a hydrogen atom or an alkyl radical and that one at least of the substituents $R_4$, $R_5$ and $R_6$ does not represent a hydrogen atom.

5 Claims, No Drawings

2-PHENYL-INDOLE DERIVATIVES

The present invention relates to 2-phenyl-indole derivatives and processes for preparing the said 2-phenyl-indole derivatives.

The 2-phenyl-indole derivatives with which the present invention is concerned are the substances represented by the formula:

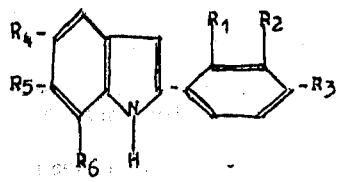

wherein $R_1$, $R_2$, $R_3$, $R_4$, $R_5$ and $R_6$, which are the same or different, represent:

$R_1 =$ a hydrogen atom or a branched- or straight-chain alkyloxy group containing from 1 to 12 carbon atoms, $R_2 =$ a hydrogen atom, a branched- or straight-chain alkyl group containing from 1 to 3 carbon atoms or a branched- or straight-chain alkyloxy group containing from 1 to 12 carbon atoms, $R_3$ and $R_5 =$ a hydrogen atom, a hydroxy group, a branched- or straight-chain alkyl group containing from 1 to 3 carbon atoms or a branched- or straight-chain alkyloxy group containing from 1 to 12 carbon atoms, $R_4 =$ a hydrogen atom, a hydroxy group, a branched- or straight-chain alkyl group containing from 1 to 3 carbon atoms or a branched- or straight-chain alkyloxy group containing from 2 to 12 carbon atoms, $R_6 =$ a hydrogen atom or a branched- or straight-chain alkyl group containing from 1 to 3 carbon atoms, with the proviso that one at least of the substituents $R_1$, $R_2$, $R_3$, $R_4$, $R_5$ and $R_6$ does not represent a hydrogen or an alkyl radical and that one at least of the substituents $R_4$, $R_5$ and $R_6$ does not represent a hydrogen atom.

The substances of formula I can be prepared, according to the Bischler Indole Synthesis, by reacting a substituted benzene derivative, represented by the formula:

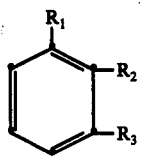

in which $R_1$, $R_2$ and $R_3$ have the same meanings as in formula I, with $ClCH_2COCl$ to form a substituted acetophenone derivative, represented by the formula:

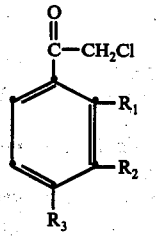

in which $R_1$, $R_2$ and $R_3$ have the same meanings as in formula I, and reacting the substances of formula III with a substituted aniline derivative, represented by the general formula:

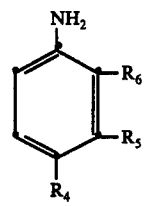

in which $R_4$, $R_5$ and $R_6$ have the same meanings as in formula I, to form the required 2-phenyl-indole derivative of formula I.

According to a variation of the Bischler Indole Synthesis, namely the Möhlau-Bischler Synthesis, the intermediate product resulting from the reaction between the compounds of formulae III and IV is isolated before the corresponding 2-phenyl-indole of formula I is obtained.

The substances of formula I may alternatively be prepared according to the Fischer Indole Synthesis, by reacting a substituted acetophenone derivative, represented by the formula:

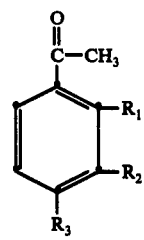

in which $R_1$, $R_2$ and $R_3$ have the same meanings as in formula I, with a substituted phenylhydrazine derivative, represented by the general formula:

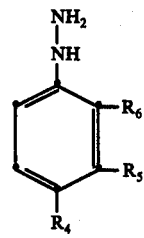

in which $R_4$, $R_5$ and $R_6$ have the same meanings as in formula I, to form a substituted acetophenone phenylhydrazone, represented by the general formula:

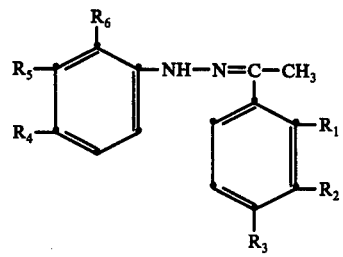

in which $R_1, R_2, R_3, R_4, R_5$ and $R_6$ have the same meanings as in formula I and cyclizing the substances of formula VII either by means of a dehydrating agent such as, for example, sulphuric acid, polyphosphoric acid or zinc chloride, or by thermomolysis, to form the required 2-phenyl-indole derivative of formula I.

The substance of formula I, wherein one at least of the substituents is a hydroxy radical, may alternatively be prepared by demethylating, by means of aluminum chloride, the corresponding methoxy-substituted 2-phenyl-indole derivative previously prepared by one of the two general methods described above.

The substances of formula I, wherein one at least of the substituents represents an alkyloxy group, may alternatively be prepared by reacting the corresponding hydroxylated 2-phenyl-indole derivative obtained in accordance with one of the two general methods described above, with an alkyl halide, in the presence of sodium methylate and N,N-dimethylformamide.

The substances of formulae II,IV,V and VI are already known or may be prepared by known procedures.

The 2-phenyl-indole derivatives according to the invention have been found to be good stabilizers of polymers and co-polymers of vinyl chloride such as, for example, polyvinyl chloride, polyvinyl chloride-polyvinyl acetate and polyvinyl choride-polyvinylidene chloride.

They have been found to be particularly valuable as stabilzers of the polymers and co-polymers intended to be formed by extrusion-moulding, blow-moulding and calendering, mainly but not solely with a view to manufacturing containers for food and drink, such as, for example, bottles for wine, oil, vinegar and mineral water.

The substances of the invention which are listed hereunder are new and are claimed as such:
2-phenyl-6-methoxy-indole (Stabilizer 1)
2-phenyl-6-hydroxy-indole (Stabilizer 2)
2-phenyl-5-dodecyloxy-indole (Stabilizer 3)
2(4'-methoxy-phenyl)-5-methyl-indole (Stabilizer 4)
2(4'-methoxy-phenyl)-7-methyl-indole (Stabilizer 5)
2-(4'-methoxy-phenyl)-6-methyl-indole (Stabilizer 6)
2-(4'-methoxy-phenyl)-5,7-dimethyl-indole (Stabilizer 7)
2(3'-methoxy-4'-hydroxy-phenyl)-7-methyl-indole (Stabilizer 8)
2-(3'-4'-methoxy-phenyl)-7-methyl-indole (Stabilizer 9)
2-(4'-methoxy-phenyl)-6,7-dimethyl-indole (Stabilizer 10)
2-(2',4'-dimethoxy-phenyl)-7-methyl-indole (Stabilizer 11)
2-(4'-dodecyloxy-phenyl)-6-methyl-indole )Stabilizer 12)
2-(3'-methoxy-4'-hydroxy-methyl)-6-methyl-indole (Stabilizer 13)
2-(3'-methyl-4'-dodecyloxy-phenyl)-7-methyl-indole (Stabilizer 14)
2(3'-methoxy-4'-hydroxy-phenyl)-5-methyl-indole (Stabilizer 15)
1(4'-methoxy-phenyl)-6-hydroxy-indole (Stabilizer 16)
2-(4' -methoxy-phenyl)-6-methoxy-indole (Stabilizer 17)
2-(4'-hydroxy-phenyl)-5-hydroxy-indole (Stabilizer 18)

Furthermore, the following substance is already known but is considered as a new stabilizer of polymers and co-polymers of vinyl chloride:
2-phenyl-5-hydroxy-indole (Stabilizer 19)

Vinyl resins are known to deteriorate under the influence of heat and it is necessary to add a stabilizing agent to these masses of synthetic matferials in order to retard thermodegradation and thus delay coloration of the resin.

Amongst the organic stabilizers used up-to-present, 2-phenyl-indole is one of the most valuable, owing to its good stabilizing power and its low toxicity. It is moreover widely used in the plastics industry to stabilize vinyl polymers an co-polymers especially those which are to be used for containing food and drink.

However, in the particular case of containers for food and drink, the stabilizer employed must not only have a low degree of toxicity but it must have high resistance to extraction from the plastic into the contents of the container.

For at least one of the above characteristics, the stabilizers of the invention have been found to be superior to 2-phenyl-indole.

The toxicity of the stabilizers of the invention was studied first and the satisfactory results obtained were such as to justify continuation of the investigation.

A. Acute toxicity

The acute toxicity (LD50) of the stabilizers listed below was measured by determining the dose of substance which provoked the death of 50% of the animals treated.

A gummy suspension of the substance under study was administered by oral route to groups of at least ten mice and the following results were observed:

| Stabilizer | LD 50 (mg/kg) | Toxic symptoms |
| --- | --- | --- |
| 3 | >5000 | none |
| 6 | >3000 | none |
| 12 | >3000 | none |

The maximal dose which does not provoke any death (LDO) was also determined for the stabilizers listed hereunder, using the same method.

The following results were observed:

| Stabilizer | LDO (mg/kg) | Toxic symptoms |
| --- | --- | --- |
| 19 | >500 | none |
| 4 | >500 | none |

B. Thermostability of the stabilized resin

The stabilizing power of the substances of the invention was studied by determining the static thermostability of the following resin:

| Ingredients | Parts by weight |
| --- | --- |
| Polyvinyl chloride resin | 100 |
| Anti-shock resin | 9 |
| Epoxide soja bean oil | 2 |
| Calcium-12-hydroxy-stearate | 0.2 |
| SL 2016 | 0.1 |
| Stabilizer | from 0.1 to 1 |

SL 2016 represents a solution of zinc-2-ethyl-hexanoate in a mixture of aromatic hydrocarbons boiling between 158° and 184° C.

The different ingredients were mixed and calendered in a mixer of which the cylinders were heated to 160° C.

The rigid sheets so obtained were then heated in a oven to a temperature of 185° or 210° C, until incipient carbonization.

A oven with a rotating drum, ventilated and equipped with a thermostat was used for this operation.

In the trials described hereinuder, the behaviour of the sheets containing one of the stabilizers to be tested was compared to that of sheets of the same formula but containing 2-phenyl-indole as stabilizer.

Comparison can be made by one of two methods, namely:

(1) The coloration of the sheets, of which samples were removed from the oven at fixed intervals, was compared to a standard scale of coloration, known as the GARDNER Scale, and expressed in terms of the reference figures of the GARDNER Scale.

Comparisons were made with a GARDNER Scale comparator which contains 18 filters of colored glass and which the possibility of observing simultaneously by transparency and in a limited field of view both the sheet and the reference filters.

It may happen that the color of the sheets is far removed from that of the GARDNER Scale, in which case comparison is difficult, if not impossible.

The following results were obtained at a temperature of 185° C, using the method described above:

| Stabilizer | Time in Minutes | | | | | | | | | | |
|---|---|---|---|---|---|---|---|---|---|---|---|
| | 0 | 6 | 12 | 18 | 24 | 30 | 36 | 42 | 48 | 54 | 60 |
| 6 | 1 | 1 | 2 | 4 | 7 | 9 | 11 | 12 | 13 | 15 | burnt |
| 7 | 1 | 1 | 3 | 6 | 12 | 14 | 15 | 15 | 16 | 18 | burnt |
| 10 | 2 | 2 | 4 | 7 | 11 | 12 | 13 | 15 | 16 | 18 | burnt |
| 2-phenyl-indole | 1 | 2 | 5 | 8 | 12 | 13 | 15 | 15 | 16 | 16 | burnt |
| 4 | 1 | 1 | 2 | 5 | 8 | 10 | 11 | 13 | 14 | 15 | burnt |
| 2-phenyl-indole | 1 | 1 | 5 | 8 | 11 | 14 | 14 | 15 | 15 | 17 | burnt |
| 9 | 1 | 1 | 3 | 6 | 10 | 11 | 11 | 15 | 15 | 18 | burnt |
| 13 | 1 | 1 | 2 | 4 | 6 | 10 | 10 | 11 | 15 | 15 | burnt |
| 2-phenyl-indole | 1 | 2 | 4 | 9 | 11 | 15 | 15 | 16 | 16 | 18 | burnt |
| 2 | 1 | 1 | 2 | 4 | 9 | 11 | 12 | 14 | 14 | 15 | 19 |
| 2-phenyl-indole | 1 | 2 | 3 | 7 | 11 | 11 | 13 | 14 | 15 | 17 | burnt |
| 17 | 1 | 1 | 2 | 4 | 8 | 10 | 11 | 12 | 14 | 17 | burnt |
| 2-phenyl-indole | 1 | 2 | 5 | 8 | 12 | 13 | 15 | 15 | 16 | 16 | burnt |
| 8 | 1 | 1 | 2 | 5 | 10 | 11 | 11 | 13 | 13 | 14 | 17 |
| 11 | 4 | 4 | 5 | 9 | 11 | 15 | 15 | 16 | 17 | burnt | burnt |
| 15 | 1 | 1 | 2 | 4 | 8 | 10 | 11 | 11 | 11 | 13 | 18 |
| 2-phenyl-indole | 1 | 1 | 4 | 5 | 10 | 11 | 13 | 13 | 15 | 15 | burnt |

(2) A simpler method which is more rapid but which nevertheless gives valid results.

A reference scale is drawn up with sheets of thermally treated polyvinyl chloride, of which the colorations have been definitely determined in GARDNER degrees as above. A GARDNER sub-scale is thus obtained in polyvinyl chloride sheets which can be directly compared to the sheets to be tested without using the comparator.

The following results were obtained with the said simplified method, the oven being heated to 210° C:

| Stabilizer | Time in Minutes | | | | | | |
|---|---|---|---|---|---|---|---|
| | 0 | 3 | 6 | 9 | 12 | 15 | 18 |
| 12 | 1 | 2 | 2 | 3 | 11 | 14 | burnt |
| 14 | 1 | 1 | 3 | 4 | 15 | 15 | burnt |
| 2-phenyl-indole | 1 | 2 | 3 | 9 | 11 | 13 | burnt |
| 3 | 1 | 1 | 2 | 3 | 6 | 11 | 15 |
| 2-phenyl-indole | 1 | 2 | 2 | 3 | 10 | 12 | burnt |
| 19 | 1 | 1 | 3 | 9 | 11 | 12 | burnt |
| 2-phenyl-indole | 1 | 1 | 3 | 10 | 12 | 19 | burnt |
| 1 | 1 | 1 | 2 | 3 | 4 | 10 | burnt |
| 2-phenyl-indole | 1 | 1 | 2 | 3 | 10 | 12 | burnt |
| 5 | 1 | 2 | 3 | 8 | 10 | 11 | burnt |
| 2-phenyl-indole | 1 | 2 | 3 | 8 | 11 | 13 | burnt |

The above results show that the tested stabilizers have a stabilizing power equal or superior to 2-phenyl-indole.

The compounds listed hereunder are superior to 2-phenyl-indole:
2-phenyl-6-methoxy-indole (Stabilizer 1)
2-phenyl-6-hydroxy-indole (Stabilizer 2)
2-phenyl-5-dodecyloxy-indole (Stabilizer 3)
2-(4'-methoxy-phenyl)-5-methyl-indole (Stabilizer 4)
2-(4'-methoxy-phenyl)-7-methyl-indole (Stabilizer 5)
2-(4'-methoxy-phenyl)-6-methyl-indole (Stabilizer 6)
2-(3'-methoxy-4'-hydroxy-phenyl)-7-methyl-indole (Stabilizer 8)
2-(4'-dodecyloxy-phenyl)-6-methyl-indole (Stabilizer 12)
2(3'-methoxy-4'-hydroxy-phenyl)6-methyl-indole (Stabilizer 13)
2-(3'-methoxyl-4'-hydroxy-phenyl)-5-methyl-indole (Stabilizer 15)
2-phenyl-5-hydroxy-indole (Stabilizer 19)

C. Extractibility of the stabilizers

The stabilizers according to the invention may be used to stabilize polymers which are intended for the manufacture of packaging and containers for food and drink and it was therefore necessary, in spite of their low toxicity, to determine their extratibility by various solvents simulating food and drink.

This study was carried out in accordance with the requirements of the Food and Drug Administration (U.S.A.).

The extractions were performed in semi-rigid bottles, prepared with the resin of which the composition is given below, and with the following solvents: water, ethanol-water 50/50, an aqueous solution of acetic acid (3%) and finally heptane.

The bottles had the following specifications:
Diameter : 62 mm
Height : 170mm
Capacity : 375ml
Weight : 28g The ratio of the volume of solvent to the surface of plastic material exposed to extraction was about 1 to 100ml of solvent, taking into account the geometric characteristics of the bottles.

| Operating conditions | |
|---|---|
| Temperature | 49° C |
| Heating | A thermostated oven for the non-inflammable solvents (water and acetic acid). A thermostated water-bath for the inflammable solvents (alcohol and heptane). |
| Duration of extraction | This is indicated under each result. These periods are, in each case, intentionally longer then those which would have given stable maximum values. |

The quantity of stabilizer extracted was determined by colorimetric assay using p-dimethylaminobenzaldehyde, in accordance with the method described in Analytical Chemistry 36,425–26 (1964).

A blank trial was carried out with a Compound of the same formula as hereunder, but without any stabilizer. A purely negative result was obtained.

The results obtained with the following formula are recorded in the Table given below:

| Ingredients | Parts by weight |
| --- | --- |
| Polyvinyl chloride resin | 100 |
| Anti-shock resin | 12 |
| Epoxide soja bean oil | 3 |
| Chelating agent | 0.25 |
| Solution of 2-ethyl-potassium-hexanoate containing 10% of potassium | 0.025 |
| Solid zinc-calcium stabilizer | 0.2 |
| Calcium stearate | 0.2 |
| Glyceryl hydroxy-stearate | 1 |
| Glyceryl trimontanate | 0.3 |
| Acrylic resin | 0.5 |
| Stabilizer | 0.3 |

Results are expressed in µg of stabilizer extracted per litre of extraction solvent or, which is the same per 1000cm² of surface extracted.

| | Solvent | | | |
| --- | --- | --- | --- | --- |
| Stabilizer | Water | Acetic-acid-water | Aqueous ethanol | Heptane |
| 2-phenyl-indole | 40 (10 days) | <3 (20 days) | 100 (9 days) | 875 (48 hours) |
| 3 | <3 (10 days) | <3 (20 days) | <10 (9 days) | 175 (48 hours) |
| 12 | <3 (10 days) | <3 (20 days) | <10 (9 days) | 175 (48 hours) |
| 14 | <3 (10 days) | <3 (20 days) | <10 (9 days) | 175 (48 hours) |

These results show that Stabilizers 3,12 and 14 are markedly less extractible than 2-phenyl-indole with regard to water, aqueous ethanol and heptane.

In the case of diluted acetic acid, the amounts extracted are approximately the same, but it is difficult to draw a conclusion because these amounts are below the sensitivity threshold of the method of assay.

With regard to water, it is clear that Stabilizer 2 is markedly superior to 2-phenyl-indole since is extractibility is at least 10 times less than that of the latter. This finding is important because it is closely related to the problem of providing containers for mineral water end the possible pollution of the latter by the container in stabilized polymer.

The following Examples provide a non-limitative illustration of the processes of preparation of the substances covered by the invention.

EXAMPLE 1

2-(4'-methoxy-phenyl(-6-methyl-indole (a) Preparation of ω-chloroparamethoxyacetophenone To a suspension of 133.3g (1mol.) of aluminum chloride and 108.1g (1mol.) of methoxybenzene in 500ml of 1,2-dichloro-ethane, were added, drop-by-drop, 112.9g (1 mol.) of monochloroacetyl cloride, the temperature of the reaction medium being maintained between 0° and 5° C.

At the end of the operation of addition, the reaction medium was allowed to return to room temperature and was then refluxed for 1 hour. After cooling, the reaction medium was poured into a mixture of water and ice. The organic phase was decanted of, dried and concentrated under vacuum.

The yellow precipitate which was obtained was filtered out, washed with water to neutrically and dried.

After recrystallizaton from ethanol, 110.4g of ω-chloroparamethoxyacetophenone were obtained.

M.P.: 96.5° C Yield - 60%

By the same method but using the appropriate starting-products, the following compounds were prepared:

| Compound | Melting Point ° C |
| --- | --- |
| ω-chloro-3-methoxy-4-hydroxy-acetophenone | 101 (toluene) |
| ω-chloro-3-methyl-4-methoxy-acetophenone | 70 (methanol) |
| ω-chloro-4-dodecyloxy-acetophenone | 61 (methanol) |

(b) Preparation of 2-(4'-methoxy-phenyl)-6-methyl-indole

A mixture comprising 374.5g (3.5mols) of 3-methyl-aniline, 3g of zinc choloride and 2g of hydroquinone was heated to a temperature of 180+ C and the temperature was then mainteined at 170° C, while 184.5g (1 mol) of ω-chloroparamethoxyacetophenone were slowly added.

At the end of the operation of addition, the reaction medium was maintained at 170° C for 30 minutes. After cooling to 90° C, the medium was hydrolized with 1 liter of a 13% aqueous solution of hydrochloric acid.

The precipitate which formed was filtered out, washed with water to neutrality, dried and recrystalized from acetone in the presence of active charcoal to give 135g of 2-(4'-methoxy-phenyl)-6-methyl-indole.

M.P.: 220° C — Yield : 57%

By the same method but using the appropriate starting-products, the following compounds were prepared:

| Compound | Melting Point ° C |
| --- | --- |
| 2-(4'-dodecyloxy-phenyl)-6-methyl-indole | 206 (acetone) |
| 2-(4'-methoxy-phenyl)-6-hydroxy-indole | 252 (toluene-acetone 50/50) |
| 2-(3'-methoxy-4'-hydroxy-phenyl)-5-methyl-indole | 196 (benzene) |
| 2-(4'-methoxy-phenyl)-6-methoxy-indole | 230 (benzene-acetone 50/50) |
| 2-(3'-methyl-4'-methoxy-phenyl)-7-methyl-indole | 135 (benzene) |
| 2-phenyl-6-methoxy-indole | 177 (ethanol) |
| 2-phenyl-5-methoxy-indole | 166 (benzene-cyclohexane 7/3) |

EXAMPLE 2

2-(4'-methoxy-phenyl)-6,7-dimethyl-indole (a) Preparation of ω-(2',3'-dimethyl-phenylamino)-4-methoxy-acetophenone A mixture comprising 500 ml of ethanol, 121g (1 mol.) of 2,3-dimethyl-aniline, 184.5g (1 mol.) of ω-chloro-4-methoxy-acetophenone and 105g (1.25 mol.) of sodium acid carbonate was refluxed for 4 hours. After cooling to 0° C, the red precipitate which formed was filtered out and carefully washed with water to neutrality. After recrysalization from a minimum of ethanol, 161.4g of ω-(2',3'-dimethyl-phenylamino)-4-methoxyacetophenone were obtained.

Yield : 60%

As this product partially decomposes when exposed to light, it was not analysed but was directly used for the following step.

By the same method but using the appropriate starting-products, the following componds were prepared:

Compound

ω-(2',3'-dimethyl-phenylamino)-4-methoxy-acetophenone

ω-(2',4'-dimethyl-phenylamino)-4-methoxy-acetophenone (b) Preparation of
2-(4'-methoxy-phenoxy-phenyl)-6,7-dimethyl-indole A mixture comprising 900 ml of silicon oil, 269g (1 mol.) of ω-(2',3'-dimethyl-phenylamino)-4-methoxy-acetophenone, 242g (2 mols) of 2,3-dimethyl-aniline, 10.1g (0.05 mol.) of 2,3-dimethyl-aniline hydrobromide and 2g of hydroquinone was slowly heated to a temperature of 200 – 220° C. The temperature was maintained for 15 minutes and the reaction medium was then cooled to 70° C. A 13% aqueous solution of hydrochloric acid was slowly added and the precipitate which formed was filtered out, washed with hexane, then with water to neutrality. After recrystallization from benzene and recrystallization twice from ethanol, 49.77g of 2-(4' -methoxy-phenyl)-6,7-dimethyl-indole were obtained.

M.P. : 148° C — Yield : 21%

By the same method but using the appropriate starting-product, the following compound was prepared:

| Compound | Melting Point ° C |
|---|---|
| 2-(4'-methoxy-phenyl)-5,7-dimethyl-indole | 177 (benzene) |

EXAMPLE 3

2-(4'-methoxy-phenyl)-7-methyl-indole

To a solution of 588g of 96% sulphuric acid were slowly added 150g (1 mol.) of 4-methoxy-acetophenone and the temperature was allowed to rise to 40 – 45° C after which 122g (1 mol.) of orthotolylhydrazine were slowly added.

At the end of the operation of addition, the reaction medium was heated to 90° C for 2 hours.

After cooling, the solution was poured into water and the precipitate was filtered out an washed with water to neutrality. After recrystallization from benzene, 35.3g of 2-(4'-methoxy-phenyl)-7-methyl-indole were obtained.

M.P. : 138° C — Yield : 15%

By the same method but using the appropriate starting-products, the following compounds were prepared:

| Compound | Melting Point ° C |
|---|---|
| 2-(2',4'-dimethoxy-phenyl)-7-methyl-indole | 109 (benzene-hexane 6/4) |
| 2-(3'-methoxy-4'-hydroxy-phenyl)-7-methyl-indole | 167 (benzene) |

EXAMPLE 4

-hydroxy-acetophenone-metamethylphenylhydrazone 2-(4'-methoxy-phenyl)-7-methyl-indole (a) Preparation of
4-methoxy-acetophenone-orthomthylphenylhydrazone A mixture comprising 800 ml of benzene, 112g (1 mol.) of orthomethylphenylhydrazine, 150g (1 mol.) of 4methoxy-acetophenone and 3ml of acetic anhydride was refluxed for 1 hour.

After cooling, the benzene solution was dried over sodium sulphate and the benzene was evaporated off under vacuum.

The 4-methoxy-acetophenone-orthomethylphenylhydrazone which was obtained was directly used for the following step, without being purified.

By th same method but using the appropriate starting-products, the following compounds were prepared:

Compound 4-methoxy-acetophenone-paramethylhydrazone
3-methoxy-4-hydroxy-acetophenone-metamethylphenyl)hydrazone (b) Preparation of
2-(4'-methoxy-phenyl)-7-methyl-indole 268g (1 mol.) of 4-methoxy-acetophenone-orthomethylphenylhydrazone were slowly added to 500 g of polyphosphoric acid (orthophosphoric acid - phosphoric anhydride 1/1), the temperature being maintained at 130° C. When the operation of addition was terminated, the temperature was maintained at 130° C for 30 minutes and the reaction medium was then cooled to about 80° – 90° C.

The reaction medium was poured into water and the precipitate was filtered off and washed with water to neutrality.

After chromotography on a silica column, with benzene as elution agent, and recrysallization from benzene, 36g of 2-(4'-methoxy-phenyl)-7-methyl-indole were obtained.

M.P. : 138° C — Yield : 15%

By the same method but using the appropriate starting-products, the following compounds were prepared:

| Compound | Melting Point ° C |
|---|---|
| 2-(4'-methoxy-phenyl)-5-methyl-indole | 251 (N,N-dimethylformamide) |
| 2-(3'-methoxy-4'-hydroxy-phenyl)-6-methyl-indole | 184 (benzene) |

EXAMPLE 5

2-phenyl-5-hydroxy-indole

A mixture comprising 1800 ml of benzene, 300g (2.25 mols) of aluminum chloride and 223g (1 mol.) of 2-phenyl-5-methoxy-indole, prepared as in Example 1, was refluxed for 2 hours.

After cooling, the suspension was poured into a mixture of 1000g of ice and 100ml of 36% hydrochloric acid.

The precipitate which formed was taken up in ether and the organic solution was washed with water to neutrality and discolored with active charcoal. After filtration, the solution was dried and ehter was evaporated off. After recrystallization from a minimum of ethanol and under nitrogen atmosphere, 185g of 2-phenyl-5-hydroxy-indole were obtained.

M.P. : 248° C — Yield : 95%

By the same method but using the appropriate starting-products, the following compounds were prepared:

| Compound | Melting Point ° C |
|---|---|
| 2-phenyl-6-hydroxy-indole | 235 (ethanol-water 8/2) |
| 2-(4'-hydroxy-phenyl)-5-hydroxy- | 280 (toluene-acetone 50/50) |

| Compound | Melting Point ° C |
|---|---|
| -continued | |
| indole | |

EXAMPLE 6

2-phenyl-5-dodecyloxy-indole

To a suspension of 67.5g (1.25 mol.) of sodium methylate in 1200ml of N,N-dimethylformamide were added 209g (1 mol.) of 2-phenyl-5-hydroxy-indole, prepared as in Example 5, the operation of addition lasting 25 minutes. The reaction medium was stirred for 25 minutes and 256g (1.25 mol.) of 1-chlorododecane were added, the operation of addition lasting 30 minutes. The reaction medium was then heated to 110° C for 7 hours.

After cooling, the solution was poured into water and the precipitate was filtered out, washed with water to neutrality and dissolved in either.

The organic solution was treated with active charcoal and dried over sodium sulphate.

The ether was evaporated off and the residue was recrystallized from cyclohexane and chromotographed on a silica column, with heptane as elution agent. Finally, it was again recrystallized from cyclohexane to give 181g of 2-phenyl-5-dodecyloxy-indole.

M.P. : 127° C — Yield : 50%

By the same method but using the appropriate starting-product, the following compound was prepared:

| Compound | Melting Point ° C |
|---|---|
| 2-(3'-methyl-4'-dodecyloxy-phenyl)-7-methyl-indole | 89 (cyclohexane) |

We claim:

1. A compound of the formula:

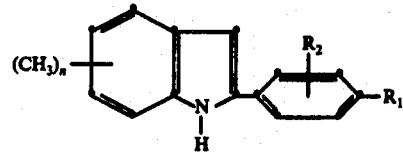

wherein $R_1$ represents a hydroxy or dodecyloxy group, $R_2$ represents a hydrogen atom, a methyl or methoxy group and $n$ is 1 or 2, with the proviso that when $R_2$ represents a hydrogen atom, $n$ is 2.

2. 2-(3'-methoxy-4'-hydroxy-phenyl)-7-methyl indole.
3. 2-(4'-dodecyloxy-phenyl)-5-methyl-indole.
4. 2-(3'-methoxy-4'-hydroxy-phenyl)-6-methyl-indole.
5. 2-(3'-methoxy-4'-hydroxy-phenyl)-5-methyl-indole.

* * * * *